United States Patent [19]

Bates

[11] Patent Number: 4,640,297

[45] Date of Patent: Feb. 3, 1987

[54] FLUID SAMPLING DEVICE

[75] Inventor: William T. D. Bates, Daventry, England

[73] Assignee: Bilbate Limited, Daventry, England

[21] Appl. No.: 694,091

[22] Filed: Jan. 23, 1985

[30] Foreign Application Priority Data

Jan. 24, 1984 [GB] United Kingdom ................ 8401754

[51] Int. Cl.⁴ ............................................. A61B 5/14
[52] U.S. Cl. ................................. 128/765; 73/864.13; 73/864.16
[58] Field of Search ....................... 128/762, 763, 765; 604/128, 187, 414, 415, 125, 218, 231; 73/864.13, 864.16-864.18; 417/437, 460

[56] References Cited

U.S. PATENT DOCUMENTS

| 984,037 | 5/1909 | Sheets | 604/125 |
| 4,257,426 | 3/1981 | Bailey | 128/765 |

Primary Examiner—Kyle L. Howell
Assistant Examiner—Randy Citrin
Attorney, Agent, or Firm—Scrivener Clarke Scrivener and Johnson

[57] ABSTRACT

A suction generating device comprises a barrel 10 within which may slide a plunger 26. A chamber 30 within the plunger is so sealed at each end that it increases in volume as the plunger is manually displaced inwardly of the barrel. An inlet 16 of the device is connected to the chamber 30 by a stem 18 so that inward movement of the plunger generates suction at the inlet 16. The device is particularly suited for single handed utilization as a blood sampling syringe or as a fluid transfer device.

7 Claims, 2 Drawing Figures

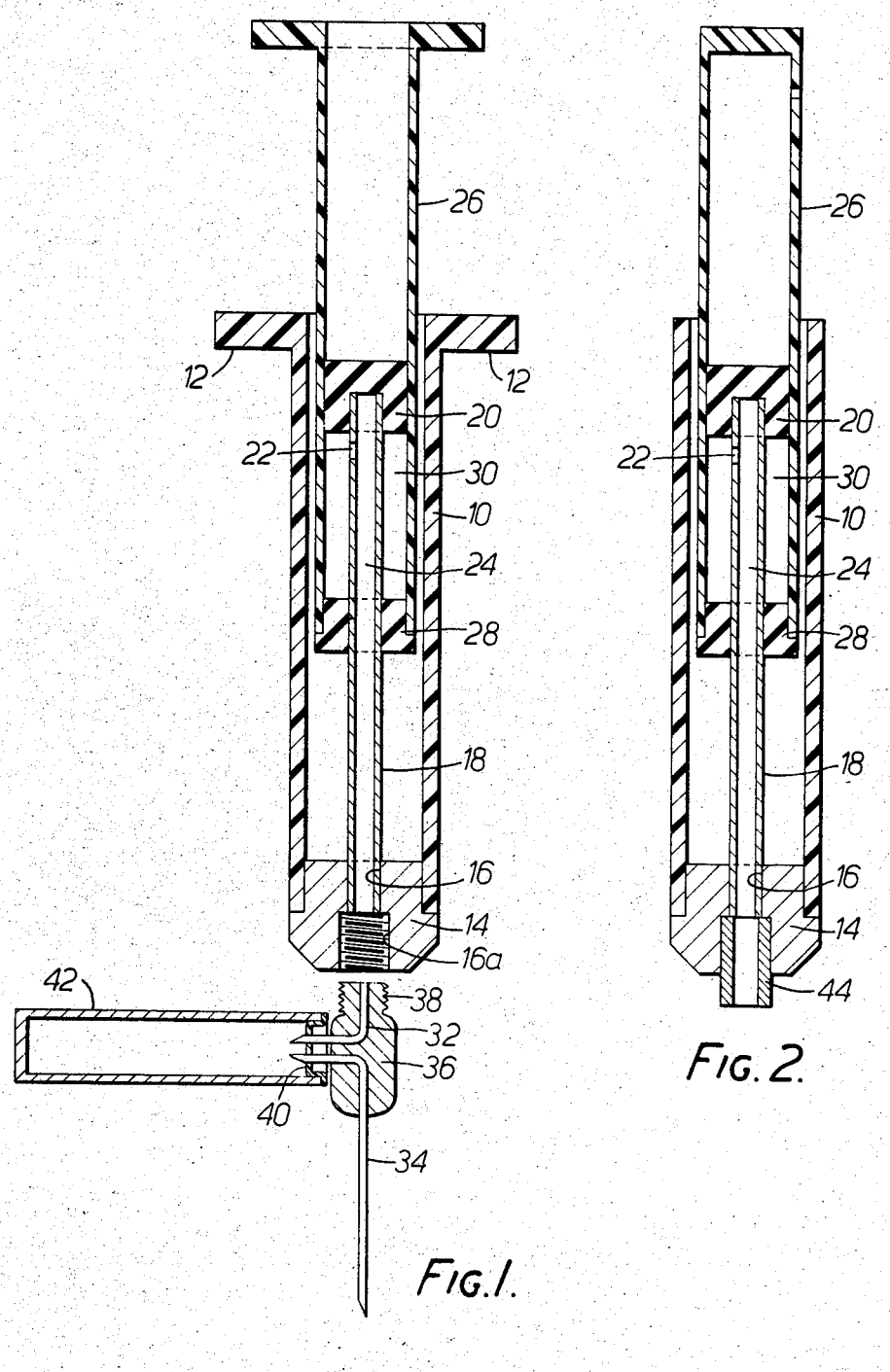

FLUID SAMPLING DEVICE

This invention relates to a suction generating device, particularly but not exclusively for use as or with a fluid sampling device. It finds particular use in the medical field, for example for taking a sample of blood from a patient or for introducing a test sample of e.g. blood into a pipette or test vessel.

It is common to introduce fluids into pipettes and the like either by exerting suction from the mouth of an operator or by allowing capillary action to draw up the fluid. Neither of these is entirely satisfactory from a number of points and it is an object of the present invention to provide a portable manually operable device to generate a controlled degree of vacuum to provide the suction necessary in these contexts.

One particular use of a device embodying the present invention is in the taking of blood samples. In order to take a sample of blood from a patient, generally a syringe fitted with a hypodermic needle is used. The operator applies one hand to steady the arm (for example) of the patient and holds the barrel of the syringe in the other hand to manipulate the syringe and thereby insert the needle tip into the patient's arm. Then the one hand must be removed from the patient in order to hold the barrel of the syringe stationary whilst the other hand is used to pull out the plunger of the syringe and thus draw blood from the patient and into a receiving chamber of the syringe. It is a disadvantage that two hands are required for this operating stage of the syringe, because sometimes it is desirable for one hand to be free to steady the arm of the patient, for example if the patient is a child.

According to a first aspect of the present invention, there is provided a suction generating device comprising a barrel and a plunger manually displaceable into said barrel to apply suction to an inlet of the device. This device enables a one-handed operation, with a thumb pressing on the outer end of the plunger and the fingers of the same hand engaged around the barrel.

When taking a sample of blood or other fluid using the known syringe, the sample is drawn into the receiving chamber of the syringe and is subsequently expelled into a test vessel by depressing the plunger again into the syringe barrel. Thus two stages of operation of the syringe are required and sometimes the time required to carry these out is undesirably long.

In accordance with a second aspect of the present invention, there is provided a fluid sampling device comprising a barrel and a plunger manually displaceable into the barrel to apply suction to an inlet of the device, said inlet being arranged for removable coupling with a test vessel such that said suction serves to draw fluid directly into said test vessel.

Embodiments to the present invention will now be more particularly described, by way of example only, with reference to the accompanying drawings in which:

FIG. 1 is a longitudinal section through a device for taking a sample of blood or other fluid from a patient; and FIG. 2 is a longitudinal section through a device for providing suction to a pipette or similar device.

Referring now to FIG. 1 of the drawings, the fluid sampling device shown comprises a cylindrical barrel 10 having a pair of oppositely-directed radial projections 12,12 at or adjacent its top, open end. Its other end is closed by a stopper member 14 inserted therein or integral therewith and having a through-bore 16. A tubular stem or connector 18 preferably of metal (e.g. stainless steel) is fixed at one of its ends into the bore 16 of stopper member 14 and extends along the axis of the barrel 10. At its other end, the stem 18 carries a first seal defined by a cylindrical end member 20 of rubber or other resilient material fixed to it so as to close its central passage 24 at this end, and the stem is formed with an aperture 22, leading into its central passage 24, just below this member 20. The sampling device further comprises a cylindrical plunger 26 which fits with clearance within the barrel 10, from the open end of the latter. The inner end of the plunger is closed by a second seal defined by a cylindrical end member 28 of rubber or other resilient material, which has a central bore slidably receiving the stem 18 as a sealing fit. The member 20 at the top of stem 18 is slidably received within the plunger itself, as a sealing fit.

It will now be seen that when the plunger is depressed into the barrel 10 (by pressing the outer end of the plunger with the user's thumb whilst the first two fingers of the same hand are engaged below the respective projections 12,12) then a chamber 30 within the plunger (lying between the first and second sealing members 20, 28 defining respective chamber end members) is progressively expanded, having the effect of creating a partial vacuum in chamber 30. Suction is thus applied through the aperture 22 of the stem 18 and along its central passage 24 to a suction inlet for the device, provided by the axial through-bore 16 of the stopper member 14. The outer portion 16a of through bore 16 may be screw-threaded as shown in FIG. 1 for removably receiving a hypodermic needle when a sample is to be taken from a patient. Alternatively a length of tubing may be attached in portion 16a when a sample is to be taken from one vessel for transfer into another; in which case the sample taken would be received in the chamber 30 and would subsequently be expelled by drawing the plunger 26 out of the barrel 10.

It is however more convenient if the interior of the device is not contacted by the fluid. To accomplish this, the sampling device inlet is arranged for removably coupling with a test vessel so that the suction which is generated (Upon depressing the plunger into the barrel) serves to draw the fluid directly into that test vessel. A first needle 32 is bent substantially at right angles and aligned with a second hypodermic needle 34 having its inner end bent substantially at a right angle. The first needle 32 has one limb co-linear with the main portion of hypodermic needle 34 so as to represent an extension thereof, whilst the other limb of needle 32 and the bent end of needle 34 are directed radially outwards to lie adjacent and parallel to each other. A body 36 of encapsulating material fixes the two needles in this configuration and is formed with a screw-threaded end 38 for coupling into the threaded bore 16a of stopper member 14 and thus connecting the axial limb of needle 32 to the axial passageway 24 of the stem 18 of the sampling device. The ends of the radially projecting portions of the two needles 32,34 are sharp so as to pierce readily a plastics top 40 of a test-tube or vessel 42. In piercing the plastics top 40, the plastics top is self-sealing with the needles around their outer surfaces.

Thus, when the needles 32,34 are pierced through the top of the test-tube 42 as shown and the body 36 is screw-threaded into the inlet 16a of the device barrel 10, the hypodermic needle 34 can be inserted into a patient and then, as the plunger is pressed into the barrel 10 causing the chamber 30 to be expanded, the suction which is applied along the inside of stem 18 is applied to the interior of test-tube 42 via the needle 32. The suction or partial vacuum thus created within test-tube 42 causes a suction to be applied through the hypodermic needle 34 so as to draw blood or other fluid from the patient and into the test-tube 42. Preferably during this operation, the tube 42 is oriented (e.g. at a suitable inclination to the horizontal) such that its top 40 is the uppermost part of the tube. The arrangement of the two needles and their encapsulating body may be disposable (i.e. intended only for a single use, then replaced). Although this arrangement is shown used with a sampling device which generates the suction upon depressing the plunger into the barrel, it might instead be used with the conventional form of syringe wherein the suction is generated upon drawing the plunger out of the barrel.

Referring now to FIG. 2, there is shown a suction generating device intended for use with pipettes and the like. Its operating principles are the same as for the fluid sampling device of FIG. 1 and where appropriate like reference numerals have been used to identify like components. The essential difference is that the inlet to the device is provided with a connection member 44, preferably of resilient material, dimensioned to fit substantially sealingly over the end of the pipette or like vessel.

Due to the method of use, it is not strictly necessary to provide the radial projections of the barrel or plunger as are shown in FIG. 1. The barrel 10 can be gripped by the fingers of the operator in the manner of gripping a dagger and the plunger depressed by the operator's thumb, as before.

In both the embodiments of the FIGS. 1 and 2, graduations may be marked on the device to indicate to an operator the degree of suction being applied. In one preferred form, a slot may be milled along the barrel, and a stop is provided to be slidable in the slot but fixable at a predetermined point of the graduated scale. The stop is shaped to contact the plunger when that has travelled a predetermined distance and thereby give a consistent suction effect. In this manner, pipettes may be filled to a desired degree or samples of predetermined volume may be taken from a patient.

I claim:

1. A suction generating device comprising a barrel, a hollow plunger having inner and outer ends and co-axially received within said barrel, means for manually moving said plunger within said barrel co-axially therewith, a first seal slideably received within said plunger intermediate the ends thereof, means fixing said first seal against movement relative to said barrel, a second seal carried by said plunger proximate its inner end and movable therewith, the space within the hollow plunger between said first and second seals defining a chamber, said plunger and seals being constructed and arranged such that inward movement of said plunger relative to said barrel causes said second seal to move away from said first seal to increase the volume of said chamber, and inlet means connected to said chamber, inward movement of said plunger to increase the volume of said chamber causing suction at the inlet means.

2. The suction generating device of claim 1 wherein said barrel receives said plunger with clearance.

3. The suction generating means of claim 1 wherein the means for fixing said first seal against movement comprises a tubular connector having an inner end fixed relative to said barrel and an outer end fixed to said first seal, said connector sealingly and slideably passing through said second seal, and means connecting said inlet means through said connector with said chamber.

4. A device according to any one of claims 1 to 3 including a separate vessel having a suction inlet, and a connector sealingly connecting said inlet means with the interior of said separate vessel.

5. A device according to any one of claims 1 to 3 wherein said inlet means includes a hypodermic needle.

6. A fluid sampling device comprising a barrel; a plunger received within the barrel and manually displaceable inwardly and outwardly with respect to said barrel; chamber means within said plunger; inlet means connected to said chamber means; a first chamber end member fixed to the plunger and movable therewith; a second chamber end member fixed in position relative to said barrel and slidably received within said plunger axially outwardly of the first chamber end member; said chamber means being defined between said first and second chamber end members, said plunger and said end members being constructed and arranged such that inward movement of the plunger relative to said barrel moves the first chamber end member relative to the second to increase the volume of said chamber means and thereby apply suction to said inlet means, and a test vessel removably coupled with said inlet means and having an inlet connectable to a supply of fluid whereby suction generated by inward displacement of said plunger relative to said barrel serves to draw fluid directly into said test vessel through its inlet.

7. A suction generating device comprising a barrel having an open end, a stopper member closing the other end of said barrel and having a bore therethrough, a tubular stem fixed at one end into the bore of said stopper member and extending into the barrel along the axis thereof, a plunger fitting with clearance within said barrel from the open end thereof and extending co-axially over said stem, a fixed sealing member closing the end of said stem remote from said stopper member and sealingly and slidably received within said plunger, a second sealing member movable with the plunger end closing the end thereof proximate to said stopper member and sealingly and slidably receiving said stem, the space in said plunger between said sealing members defining a collapsible and expansible chamber, and an aperture in said stem adjacent said fixed sealing member and connecting the interior of said stem with said chamber.

* * * * *